United States Patent [19]

Fujioka et al.

[11] Patent Number: 5,401,754
[45] Date of Patent: Mar. 28, 1995

[54] AGENT FOR TREATING THROMBOSIS AND PHOSPHODIESTERASE INHIBITOR

[75] Inventors: Takafumi Fujioka; Shuji Teramoto; Michiaki Tominaga; Yoichi Yabuuchi, all of Tokushima, Japan

[73] Assignee: Otsuka Pharmaceutical Company, Limited, Tokyo, Japan

[21] Appl. No.: 208,803

[22] Filed: Mar. 11, 1994

Related U.S. Application Data

[63] Continuation of Ser. No. 984,495, Dec. 2, 1992, abandoned.

[30] Foreign Application Priority Data

Apr. 3, 1991 [JP] Japan .................. 3-070223
Feb. 6, 1992 [JP] Japan .................. 4-021137

[51] Int. Cl.$^6$ .............................................. A61K 31/47
[52] U.S. Cl. .................................................. 514/312
[58] Field of Search ...................................... 514/312

[56] References Cited

U.S. PATENT DOCUMENTS

| | | | |
|---|---|---|---|
| 3,969,507 | 7/1976 | Kohri ................. | 514/312 |
| 4,277,479 | 7/1981 | Nishi et al. ........... | 514/312 |
| 4,298,739 | 11/1981 | Nishi et al. ........... | 546/158 |
| 4,389,392 | 6/1983 | Adachi ................ | 424/1 |
| 5,053,514 | 10/1991 | Fujioka et al. ........ | 546/157 |

FOREIGN PATENT DOCUMENTS

| | | |
|---|---|---|
| 0355583 | 2/1990 | European Pat. Off. . |
| 49-51271 | 5/1974 | Japan . |
| 50-142576 | 11/1975 | Japan . |
| 52-108980 | 9/1977 | Japan . |
| 54-30184 | 3/1979 | Japan . |
| 55-129268 | 10/1980 | Japan . |
| 56-8319 | 1/1981 | Japan . |
| 57-14574 | 1/1982 | Japan . |
| 57-80322 | 5/1982 | Japan . |
| 57-93962 | 6/1982 | Japan . |

OTHER PUBLICATIONS

Toyoki Mori et al, *The Japanese Journal of Pharmacology*, The 64th Annual Meeting, Mar. 24–27, 1991, p. 45P.

Fujioka et al, The Pharmaceutical Society of Korea, *International Congress of New Drugs Development* "Programs and Abstracts", Aug. 18–24, 1991, pp. 44 and 203.

Hiroyuki Fujiki et al, *The Japanese Journal of Pharmacology*, The 64th Annual Meeting, Mar. 24–27, 1991, p. 158P.

Hosokawa et al, Cardiovascular Actions of OP-C-18790: A Novel Positive Inotropic Agent with Little Chronotropic Action, *Heart Vessels*, 7:66–75, (1992).

*Primary Examiner*—Raymond J. Henley, III
*Assistant Examiner*—William R. A. Jarvis
*Attorney, Agent, or Firm*—Sughrue, Mion, Zinn, Macpeak & Seas

[57] ABSTRACT

A pharmaceutical preparation comprising at least one compound selected from the group consisting of carbostyril derivatives having the general formula:

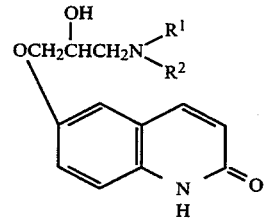

wherein $R^1$ is hydrogen or a lower alkyl group optionally having hydroxy group as a substituent; $R^2$ is a phenyl(lower alkyl) group optionally having 1 to 3 substituents selected from the group consisting of a lower alkoxy group and a halogen atom on the phenyl ring, pyridyl(lower alkyl) group, or a group of the formula —A—$NR^3R^4$ (wherein A is a lower alkylene group, $R^3$ and $R^4$ are the same or different and represent a lower alkyl group or phenyl group), and a salt thereof, which is useful as an agent for treating thrombosis, more particularly, as an agent for inhibiting platelet aggregation and as an agent for platelet aggregate dissociation.

13 Claims, No Drawings

AGENT FOR TREATING THROMBOSIS AND PHOSPHODIESTERASE INHIBITOR

This is a Continuation of Parent application Ser. No. 07/984,495, filed Dec. 2, 1992, now abandoned.

TECHNICAL FIELD

The present invention relates to an agent for treating thrombosis and a phosphodiesterase inhibitor comprising as an active ingredient a carbostyril derivative or a salt thereof.

BACKGROUND ART

A carbostyril derivative having the general formula (1):

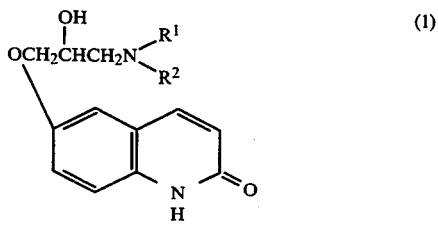

wherein $R^1$ is hydrogen or a lower alkyl group optionally having hydroxy group as a substituent; $R^2$ is a phenyl(lower alkyl) group optionally having 1 to 3 substituents selected from the group consisting of a lower alkoxy group and a halogen atom on the phenyl ring, pyridyl(lower alkyl) group, or a group of the formula $-A-NR^3R^4$ (wherein A is a lower alkylene group, $R^3$ and $R^4$ are the same or different and represent a lower alkyl group or phenyl group), or a salt thereof, is a known compound which is described in, for example, EP Publication No. 355583 to be useful as cardiotonics. These compounds are also known to be useful as antihistamines (Japanese Patent First Publication No. 8319/1981). In addition, among the compounds represented by the above general formula, 6-[3-(3,4-dimethoxybenzylamino-2-hydroxypropoxy)-2-(1H)-quinoline compound (the compound of the formula (1) wherein $R^1$ is hydrogen, $R^2$ is 3,4-dimethoxybenzyl group; OPC-18790) has an inotropic activity and is useful as an agent for treating heart failure (The Japanese Journal of Pharmacology, The 64th Annual Meeting, March 1991, Kobe, Japan and International Congress of New Drug Development, August 1991, Seoul, Korea).

The present inventors have intensively studied the above-mentioned carbostyril derivative and a salt thereof, and as a result, have found that said compound shows an excellent platelet aggregation inhibitory activity, phosphodiesterase inhibitory activity, cerebral blood flow increasing activity and platelet aggregate dissociation activity, and is useful as an agent for treating thrombosis and as a phosphodiesterase inhibitor. Thus, the present invention has been completed.

DISCLOSURE OF THE INVENTION

That is, the present invention relates to agents for treating thrombosis, phosphodiesterase inhibitors, platelet aggregation inhibitors, ameliorants of cerebral circulation and platelet aggregate dissociation agents comprising at least one of the carbostyril derivatives represented by the above general formula (1) and salt thereof.

The phosphodiesterase inhibitor of the present invention has an inhibitory activity specifically against those phosphodiesterases which decompose cyclic adenosine monophosphate (hereinafter referred to as "C-AMP").

A substance showing the activity to inhibit the C-AMP decomposing enzyme, phosphodiesterase (hereinafter referred to as "PDE"), is useful for prevention or treatment of various diseases in which C-AMP is decreased due to metabolic disorder of C-AMP as described in, for example, Annual Review of Pharmacology and Toxicology, Vol. 17, pp 441–477 (1977). That is, the intracellular C-AMP is known to be a biosubstance which is produced from adenosine triphosphate (hereinafter referred to as "ATP") via adenylate cyclase by the sympathetic neural transmitter such as catecholamines and various peptide hormones, and is decomposed by PDE. Said C-AMP not only transmits the activity of bioamines and peptide hormones into cells but also effects on cell division, growth and differentiation of fertilization and conception, tension of smooth muscle, contraction and metabolism of heart, the function of central and autonomic nervous systems, immune reaction, generative function, release of substances contained in the intracellular storage granules such as insulin, histamine, serotonin, etc., lysosome enzyme system, and the like. The metabolic disorder (decrease) of said C-AMP is closely related to various diseases such as, for instance, the outbreak of cancer, bronchial asthma, diabetes, arteriosclerosis, circulation failure, hypertension, psychosis, psoriasis, and the like, and the use of PDE inhibitors specific to said C-AMP is effective for treatment or prevention of these diseases. Among the PDE inhibitors, those inhibitors of PDE specific to the above-mentioned C-AMP is especially effective, which is described in, for example, Molecular Pharmacology, Vol. 13, pp 400–406 (1976).

Accordingly, the PDE inhibitor of the present invention is useful as an agent for prevention and/or treatment of the following various diseases.

Advances in Cyclic Nucleotide Research Vol. 1, pp 175 (1972) and Molecular Pharmacology Vol. 6, pp 597 (1970) disclose that the PDE inhibitor acted on the smooth muscle of blood vessel increases the C-AMP content therein to expand said smooth muscle, and hence, the PDE inhibitor improves blood flow conditions. From this, the PDE inhibitor is useful as ameliorants of circulation, especially as ameliorants of cerebral circulation.

There has been reported that the C-AMP content is decreased in arterial lesions of spontaneous hypertension rat (hereinafter referred to as "SHR"), which is due to increase of the PDE activity and attenuation of adenylate cyclase activity for vasolidative stimuli [Science Vol. 179, pp 807 (1973)]. This seems to worsen the relaxation reaction of the smooth muscle of blood vessel. Therefore, hypertension can be treated by inhibiting PDE and increasing C-AMP to decrease the blood vessel resistance.

In addition, in renal hypertension, etc., diuretics is used for decreasing the total amount of blood and thereby showing the activity to lower the blood pressure. There are reports that the known diuretics, benzothiazide derivative, has PDE inhibitory activity [cf. Annals of New York Academy of Science, Vol. 150, pp 256 (1968)] and the increase of C-AMP accelerates the diuretic activity [cf. Journal of Clinical Investigation, Vol. 41, pp 702 (1968)]. Therefore, the PDE inhibitor is useful as anti-hypertensions and as diuretics.

As described in Proceedings of the National Academy of Science of United States of America, Vol. 68, pp 425 (1971), the known PDE inhibitor, theophyline, shows the activity to normalize cancerated and cancerized cells, and from this, it is understood that the PDE inhibitor of the present invention is effective as an agent for treating cancer.

Journal of Clinical Investigation, Vol. 52, pp 48 (1973) discloses that relaxation of the bronchial smooth muscle is induced by increase of the C-AMP content by the β-action of the sympathetic neural transmitter, catecholamine, and the C-AMP content in the bronchial smooth muscle in patients suffering from bronchial asthma generally tends to decrease. The PDE inhibitor allows for increase of said C-AMP content and thereby relaxation of the bronchial smooth muscle by inhibiting decomposition of C-AMP. In fact, the known PDE inhibitor, theophyline, is known to be an agent for treating bronchial asthma due to such an action mechanism. Accordingly, the PDE inhibitor of the present invention is also useful as an agent for treating bronchial asthma.

As reported in Journal of Immunology, Vol. 108, pp 695 (1972), patients suffering from allergic asthma show contraction of the bronchial smooth muscle due to release of the chemical transmitter, histamine, from the mast cells, and the like. The release of histamine from the mast cells as mentioned above is induced by decrease of C-AMP, and hence, the PDE inhibitor can inhibit the above histamine release by increasing said C-AMP content and is effective for treatment or prevention of allergic asthma.

As shown in Cyclic Nucleotides in Disease, Boltimore, Univ. Parkpress, pp 211 (1975), the most important hormone for lowering the blood sugar is insulin. Secretion of said insulin is accelerated by glucose, catecholamine, glucagon, etc. Prior to this secretion, the C-AMP level is increased. The increase of C-AMP in pancrea can effect on acceleration of insulin secretion. Accordingly, the use of the PDE inhibitor is effective for increase of C-AMP, acceleration of insulin secretion and thereby the treatment of diabetes.

Japanese Heart Journal, Vol. 16, pp 76 (1975) discloses that the C-AMP content is decreased in intravascular endothelial cells with arteriosclerosis and conversely increase of the C-AMP content accelerates lipolysis activity. The PDE inhibitor increases the C-AMP content and accelerates lipolysis in intravascular endothelial cells, and hence, is effective for prevention of arteriosclerosis.

As described in Federation Proceedings, Vol. 30, pp 330 (1971), pharmacological antipsychotics changes the C-AMP content in the central nervous system, which is the site where the drug acts mainly. For example, the phenothiazines antipsychotics increases the C-AMP level in cells by inhibiting the activation of PDE by calcium depending activator protein and the tricyclic antidepressants benzazepines have PDE inhibitory activity in brain and thereby are effective for treatment of psychosis. Accordingly, the PDE inhibitor can be utilized for treatment of psychosis induced by the decrease of C-AMP level like these antipsychotics.

As described in Journal of Investigative Dermatology, Vol. 64, pp 124 (1975), psoriasis quickly spread over the skin, and in the focus of psoriasis, the C-AMP content is decreased, the PDE activity is increased by about 3-folds as compared to the normal value and the content of cyclic guanine monophosphate (hereinafter referred to as "C-GMP") is increased. In addition, glycogen pool is also observed. C-AMP inhibits proliferation and differentiation of cells and accelerates glycolysis. For the treatment of psoriasis, the clinically known PDE inhibitor, papaverine, has been actually used and hence the PDE inhibitor is effective as an agent for treatment of said disease.

As described in Hiroshima University Igaku Zasshi, Vol. 36, No. 6, pp 688–689 (1988), a substance increasing the CAMP content in ciliaris epithelium decreases the amount of aqueous humor produced from ciliaris epithelium and thereby lowers the intraocular pressure. The intraocular pressure has been lowered by administration of the PDE inhibitor, and hence, the PDE inhibitor is effective as an agent for lowering the intraocular pressure.

The carbostyril derivatives having the above general formula (1) and the salt thereof have an excellent platelet aggregation inhibitoryactivity, phosphodiesterase inhibitory activity, cerebral blood flow increasing activity, platelet aggregate dissociation activity, thromboxane $A_2$ antagonistic activity, and the like. Accordingly, said carbostyril derivatives and the salt thereof can be used suitably as an agent for prevention and treatment of thrombosis such as cerebral apoplexy, cerebral infarction, myocardial infarction, etc., ameliorants of cerebral circulation, phosphodiesterase inhibitor, and an agent for treatment of glaucoma.

Each group in the above general formula (1) is shown more specifically as follows:

The lower alkyl group includes a straight chain or branched chain alkyl group having 1 to 6 carbon atoms such as methyl, ethyl, propyl, isopropyl, butyl, tert-butyl, pentyl, hexyl, etc.

The phenyl(lower alkyl) group optionally having 1 to 3 substituents selected from the group consisting of a lower alkoxy group and a halogen atom on the phenyl ring includes a phenylalkyl group optionally having 1 to 3 substituents selected from the group consisting of a straight chain or branched chain alkoxy group having 1 to 6 carbon atoms and a halogen atom on the phenyl ring wherein the alkyl moiety is a straight chain or branched chain alkyl group having 1 to 6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, di-phenylmethyl, 2,2-diphenylethyl, 2-(3-methoxyphenyl)ethyl, 1-(4-methoxyphenyl)ethyl, 2-methoxybenzyl, 3-(2-ethoxyphenyl)propyl, 4-(3-ethoxy-phenyl)-butyl, 1,1-dimethyl-2-(4-ethoxyphenyl)ethyl, 5-(4-isopropoxyphenyl)pentyl, 6-(4-hexyloxyphenyl)hexyl, 3,4-dimethoxybenzyl, 3,4,5-trimethoxybenzyl, 2,5-dimethoxybenzyl, 2-chlorobenzyl, 2-(3-bromophenyl)ethyl, 1-(4-chlorophenyl)ethyl, 3-(4-fluorophenyl)propyl, 4-(2,3-dichlorophenyl)butyl, 1,1-dimethyl-2-(2,4-dibromophenyl)ethyl, 5-(3,4-difluorophenyl)pentyl, 6-(2,4,6-trichlorophenyl)hexyl, 2-methyl-3-(2-fluorophenyl)propyl, 2-chloro-4-methoxybenzyl, 3-methoxybenzyl, 4-methoxybenzyl, 3-chlorobenzyl, 4-chlorobenzyl, and the like.

The pyridyl(lower alkyl) group includes those pyridylalkyl groups wherein the alkyl moiety is a straight chain or branched chain alkyl group having 1 to 6 carbon atoms, such as (3-pyridyl)-methyl, (2-pyridyl)-methyl, 2-(4-pyridyl)ethyl, 1-(2-pyridyl)ethyl, 3-(2-pyridyl)propyl, 4-(2-pyridyl)ethyl, 1,1-dimethyl-2-(3-pyridyl)ethyl, 5-(2-pyridyl)pentyl, 6-(4-pyridyl)hexyl, and the like.

The lower alkylene group includes a straight chain or branched chain alkylene group having 1 to 6 carbon atoms such as methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, and the like.

The lower alkyl group optionally having hydroxy group as a substituent includes a straight chain or branched chain alkyl group having 1 to 6 carbon atoms optionally having hydroxy group as a substituent, such as methyl, ethyl, propyl, isopropyl, butyl, tert-butyl, pentyl, hexyl, hydroxymethyl, 2-hydroxyethyl, 1-hydroxyethyl, 3-hydroxypropyl, 4-hydroxybutyl, 1,1-dimethyl-2-hydroxyethyl, 5-hydroxypentyl, 6-hydroxyhexyl, 2-methyl-3-hydroxypropyl, and the like.

The carbostyril derivative represented by the general formula (1) of the present invention can easily be converted into an acid addition salt by treating with a pharmaceutically acceptable acid. Said acid includes, for example, an inorganic acid such as hydrochloric acid, sulfuric acid, phosphoric acid, hydrobromic acid, etc., an organic acid such as oxalic acid, maleic acid, fumaric acid, malic acid, tartaric acid, citric acid, benzoic acid, etc.

Among the carbostyril derivative represented by the general formula (1) of the present invention, those compounds having an acidic group can easily be converted into a salt by treating with a pharmaceutically acceptable basic compound. Said basic compound includes, for example, sodium hydroxide, potassium hydroxide, calcium hydroxide, sodium carbonate, potassium hydrogen carbonate, and the like.

The present invention includes, of course, an optical isomer.

The compound of the general formula (1) is usually used in the form of the conventional pharmaceutical preparation. The pharmaceutical preparation is prepared using conventional diluents or vehicles such as fillers, thickening agents, binders, wetting agents, disintegrators, surfactants, lubricants, etc. The pharmaceutical preparation may be in various dosage forms depending on the therapeutical purpose and such dosage form includes typically tablets, pills, powders, solutions, suspensions, emulsions, granules, capsules, suppositories, injections (solutions, suspensions, etc.), and the like. For formulating into tablets, the carriers known in the field can widely be used, including, for example, vehicles such as lactose, sucrose, sodium chloride, glucose, urea, starch, calcium carbonate, kaolin, crystalline cellulose, silic acid, etc.; binders such as water, ethanol, propanol, simple syrup, a glucose solution, a starch solution, a gelatin solution, carboxymethyl-cellulose, shellac, methylcellulose, potassiumphosphate, polyvinylpyrrolidone, etc.; disintegrators such as dried starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, lactose, etc.; disintegration inhibiting agents such as sucrose, stearin, cacao butter, hydrogenated oil, etc.; absorption promoting agents such as quaternary ammonium salt, sodium lauryl sulfate, etc.; wetting agents such as glycerol, starch, etc.; absorbants such as starch, lactose, kaolin, bentonite, colloidal silic acid, etc.; lubricants such as purified talc, stearate, boric acid powder, polyethylene glycol, etc., and the like. In addition, tablets may also be in the form of the conventional coated tablet, including sugar coated tablets, gelatin coated tablets, enteric coated tablets, film coated tablets, or double-layered tablets, multilayer tablets. For formulating into pills, the carriers known in the field can widely be used, including, for example, vehicles such as glucose, lactose, starch, cacao butter, hydrogenated vegetable oil, kaolin, talc, etc.; binders such as acacia powder, powdered tragacanth, gelatin, ethanol, etc.; disintegrators such as laminaran, agar, etc., and the like. For formulating into suppositories, the carriers known in the field can widely be used, including, for example, such as polyethylene glycol, cacao butter, higher alcohols, esters of higher alcohols, gelatin, semisynthesized glyceride, etc. For preparation of injections, the solutions or suspensions are sterilized and are preferably isotonic to blood. For formulating into these solutions, pills and suspensions, any conventional diluent known in the field can be used, including, for example, water, ethyl alcohol, propylene glycol, ethoxylated isostearyl alcohol, polyoxylated isostearyl alcohol, polyoxyethylene sorbitan fatty acid esters, and the like. In this case, the pharmaceutical preparation of the present invention may contain salt, glucose or glycerol in an amount sufficient for preparing the isotonic solution. The pharmaceutical preparation may also contain conventional solubilizing agents, buffers, anesthetizing agents and the like. Said pharmaceutical preparation may further contain optionally coloring agents, preservatives, flavoring agents, perfumes, sweetening agents, etc. and other drugs.

The amount of the compound of the general formula (1) contained in the pharmaceutical preparation of the present invention is not particularly limited and selected from the wide range and usually from 1 to 70% by weight, preferably from 1 to 30% by weight based on the total amount of the composition.

The administration route of the pharmaceutical preparation of the present invention is not particularly limited and determined depending on dosage forms, age and sex or other conditions of patients, severity of the disease, and the like. For example, tablets, pills, solutions, suspensions, emulsions, granules and capsules are orally administered. The injections are intravenously administered solely or together with the conventional auxiliary liquid such as glucose, amino acid, etc. or, if necessary, administered intramuscularly, intradermally, subcutaneously or intraperitoneally. The suppositories are administered intrarectally.

The dosage amount of the pharmaceutical preparation of the present invention is suitably determined depending on usage, age, sex or other conditions of patients, severity of the disease, and the like. The amount of the compound of the general formula (1) as the active ingredient is usually administered in an amount of about 0.1 to 10 mg per 1 kg of body weight per day. The dosage unit preferably contains the active ingredient in an amount of 1 to 200 mg.

BEST MODE FOR CARRYING OUT THE INVENTION

Pharmacological test results and Examples of Preparations are shown below.

Pharmacological test 1

The platelet aggregation inhibitory activity of test compounds was measured in accordance with the method of Born et al. [J. Physiol., London, 162, 67, (1962)] using a platelet aggregator [Platelet Aggregation Tracer manufactured by Niko Biosceince K.K.].

To 9 volumes of blood taken from human beings was added 1 volume of 3.8% citric acid and this sample was centrifuged at 1100 rpm for 10 minutes to give a platelet rich plasma (PRP). The remaining sample was further centrifuged at 3000 rpm for 15 minutes to give a platelet poor plasma (PPP).

The platelets in the PRP obtained above was counted using Coulter Counter, Coulter electronics inc. and diluted to 300000 platelets/µl with the PPP to prepare a PRP solution.

A cell for measurement of aggregation was charged with a solution containing a fixed concentration of test compounds (1 to 2 µl) and the PRP solution prepared above (200 µl) and warmed at 37° C. for 1 minute. Then, to the cell was added a suspension of adenosine diphosphate (ADP, manufactured by Sigma) or collagen (Collagen Reagent Horm, manufactured by Hormon-Chemie) to induce platelet aggregation and the transparency of the cell was measured and a platelet aggregation curve was prepared. The final concentration of the above ADP and the collagen was adjusted to 14 to 16 µM and 1 to 4 µg/ml, respectively.

Maximum Aggregation Rate (MAR) of platelets was calculated from the platelet aggregation curve by the following formula:

$$MAR = (b-a)/(c-a) \times 100$$

wherein (a) represents the transparency of PRP measured in the similar test, (b) represents the transparency of the PRP solution containing the test compound and the aggregation inducer at the time of maximum change in the above test, and (c) represents the transparency of the PPP solution measured in the similar test.

MAR for control with no addition of the test compound was also calculated, and based on this value, the platelet aggregation inhibitory rate (%) of each test compound at various concentrations in the above test was calculated from the following formula:

Inhibitory rate = [1 − (MAR of PRP with addition of test compound)/(MAR of PRP with no addition of test compound)] × 100

Pharmacological test 2

C-AMP phosphodiesterase inhibitory activity of the compound of the present invention was measured in accordance with the method described in Biochimica et Biophysica Acta, Vol. 484, pp 398–407 (1977) and Biochemical Medicine, Vol. 10, pp 301–311 (1974).

That is, the heart taken out from dog was put in a solution (pH 6) containing 2-mercaptoethanol (3.75 mmol) in Tris-acetate buffer (50 mmol) at 4° C. and the blood vessels and the like were removed. The heart was minced in 3 volumes of the buffer and ground with a homogenizer. After repeating freezing and thawing twice, the product was centrifuged at 105000 × g to give a supernatant which was used as a crude enzyme solution.

The crude enzyme solution (10 ml) was passed through DEAE-cellulose column buffered with a solution (pH 6) containing 2-mercaptoethanol (3.75 mmol) in Tris-acetate buffer (50 mmol) and washed and eluted with the same buffer (30 ml). Elution was conducted with sodium acetate-Tris-HCl buffer by the linear gradient method at a flow rate of 0.5 ml/minute to give fractions of each 5 ml (total amount of elution: about 300 ml). Thereby, there was obtained a fraction which showed a weak activity of not more than 2 nmol/ml/minute at a higher concentration of C-AMP substrate of 100 µmol and a strong activity of not less than 100 pmol/ml/minute at a lower concentration of C-AMP substrate of 0.4 µmol and this fraction was used as C-AMP phosphodiesterase.

An aqueous solution (0.1 ml) containing various concentrations of test compound was mixed with Tris-HCl buffer (pH 8.0, 40 mmol, containing calf serum albumin 50 µg and $MgCl_2$ 4 mmol) containing C-AMP (tritium C-AMP)(0.4 µmol) to prepare a substrate solution (0.2 ml).

To the above substrate solution was added the C-AMP phosphodiesterase solution (0.2 ml) and the mixture was reacted at 30° C. for 20 minutes to convert tritium C-AMP into tritium 5'-AMP. After the reaction solution was dipped into a boiling water to quench the reaction, it was cooled in ice-water. Thereto was added snake venom (1 mg/ml)(0.05 ml) and the reaction was conducted at 30° C. for 10 minutes to convert the tritium 5'-AMP into tritium adenosine. The reaction solution was passed through a cation exchange resin to absorb the tritium adenosine, which was washed with distilled water and eluted with 3N aqueous ammonia (1.5 ml). The eluate was measured for the produced tritium adenosine using the conventional liquid scintillation counter and thereby the phosphodiesterase activity was measured.

From the above results, the phosphodiesterase activity of the test compound at various concentrations (Vs) was obtained, and using this value and the activity value of control (water without the test compound), a phosphodiesterase inhibitory rate (%) was calculated in accordance with the following formula:

Phosphodiesterase inhibitory rate
(%) = $(Vc - vs)/vc \times 100$

Pharmacological Test 3

A hybrid dog was anesthetized with pentobarbital (30 mg/kg i.v.) and the chest was opened under artificial respiration. The topical blood flow (the blood flow in the cerebellum and the brain) was determined in the following manner. That is, about 600 million colored microspheres were introduced into the left atrium and then various amounts of the test compound was continuously administered intravenously over 30 minutes. After administration of each dosage, about 600 million colored microspheres having a distinctive color for each dosage were administered at the left atrium. Thereafter, the cerebellum and the brain were taken out and treated with an alkali to extract the colored microspheres from the tissue. The collected colored microspheres were counted for each color under a microscope and a local blood flow was calculated by comparing with the colored microspheres in arterial blood using the following formula:

$$Qm = (Cm \times Qr)/Cr$$

wherein Qm means the topical blood flow, Cm means the number of microspheres per 1 g of the tissue, Qr means a rate of collection of arterial blood, and Cr means the number of microspheres.

Increasing rate of blood flow (%) was calculated in accordance with the following formula:

Increasing rate of blood flow
$(\%) = [(Qmd - Qmc)/Qmc] \times 100$ wherein Qmd means the topical blood flow when the test compound was administered, and Qmc means the topical blood flow when the test compound was not administered.

Pharmacological Test 4

In the same manner as in the above test 1, the obtained PRP solution (200 μl) was put in cell for measurement of aggregation and the cell was warmed at 37° C. for 1 minute. Thereto was added ADP or collagen suspension (final concentration of 14 to 16 μM and 1 to 4 μg/ml, respectively) without addition of the test compound to form aggregates of platelet. MAR was determined after stable transparency was obtained. This MAR was referred to as "MAR-1". Then, the test compound was added and MAR was determined from the transparency after 5 minutes. This MAR was referred to as "MAR-2".

Platelet aggregate dissociation rate (%) was calculated in accordance with the following formula:

Platelet aggregate dissociation rate
$(\%) = [(\text{MAR-1}) - (\text{MAR-2})]/(\text{MAR-1}) \times 100$ The test compounds used in the above tests are as follows:

Test Compound No.
1. 6-[3-(N-methyl-N-benzylamino)-2-hydroxypropoxy]-carbostyril
2. 6-[3-(3-methoxybenzyl)amino-2-hydroxypropoxy]-carbostyril hydrochloride
3. 6-[3-(4-chlorobenzylamino)-2-hydroxypropoxy]carbostyril hydrochloride
4. 6-{3-[N-methyl-N-(2-pyridylmethyl)amino]-2-hydroxypropoxy}carbostyril
5. 6-[3-{N-methyl-N-[2-(N-methylanilino)ethyl]amino}-2-hydroxypropoxy]carbostyril
6. 6-[3-(4-methoxybenzylamino)-2-hydroxypropoxy]-carbostyril hydrochloride
7. 6-[3-(3,4-dimethoxybenzyl)amino-2-hydroxypropoxy]carbostyril
8. 6-[3-(3-chlorobenzyl)amino-2-hydroxypropoxy]carbostyril
9. 6-[3-(3,4-diethoxybenzyl)amino-2-hydroxypropoxy]-carbostyril
10. 6-{3-[N-(2-hydroxyethyl)-N-(4-fluorobenzyl)amino]-2-hydroxypropoxy}carbostyril The results of Pharmacological tests 1, 2, 3 and 4 are shown in the following Tables 1, 2, 3 and 4, respectively.

TABLE 1

| Test compound No. | Platelet aggregation inhibitory rate (%) | | | | | |
|---|---|---|---|---|---|---|
| | ADP | | | Collagen | | |
| Conc. (mol) | $10^{-4}$ | $10^{-5}$ | $10^{-6}$ | $10^{-4}$ | $10^{-5}$ | $10^{-6}$ |
| 1 | 79.0 | 31.7 | 14.9 | 96.3 | 70.7 | 3.8 |
| 2 | 89.1 | 43.9 | 14.9 | 97.2 | 95.7 | 23.1 |
| 3 | 78.2 | 44.5 | 13.2 | 97.8 | 96.7 | 17.0 |
| 4 | 77.5 | 30.5 | 13.5 | 97.2 | 64.3 | — |
| 5 | 84.8 | 38.4 | 21.6 | 96.5 | 72.9 | 44.4 |
| 6 | 77.5 | 43.8 | 7.4 | 97.0 | 96.7 | 17.0 |
| 7 | 96.4 | 39.0 | 9.5 | 96.9 | 91.6 | 4.1 |
| 8 | 62.0 | 27.4 | 5.1 | 93.1 | 27.7 | 12.3 |

TABLE 2

| Test compound No. | Phosphodiesterase inhibitory rate (%) | |
|---|---|---|
| Conc. (mol) | $10^{-4}$ | $10^{-5}$ |
| 2 | 2.32 | 48.63 |
| 3 | 32.46 | 86.11 |
| 7 | 15.27 | 72.39 |
| 9 | 50.63 | 89.07 |
| 10 | 23.90 | 74.63 |

TABLE 3

| Test comp. No. | Organ where blood flow was measured | Dosage (μg/kg/min) | Increasing rate of blood flow (%) |
|---|---|---|---|
| 7 | Cerebellum | 3 | 15.2 ± 11.5 |
| | | 10 | 29.7 ± 11.5 |
| | Brain | 3 | 25.9 ± 7.0 |
| | | 10 | 57.8 ± 10.9 |

TABLE 4

| Test compound No. | Platelet aggregate dissociation rate (%) | | | | | |
|---|---|---|---|---|---|---|
| | ADP | | | Collagen | | |
| Conc. (μmol) | 10 | 30 | 100 | 10 | 30 | 100 |
| 7 | 41.5 | 43.3 | 71.7 | 13.3 | 26.7 | 28.0 |

Preparation Example 1

| 6-[3-(3-Methoxybenzyl)amino-2-hydroxypropoxy] carbostyril hydrochloride | 5 mg |
|---|---|
| Starch | 132 mg |
| Stearate magnesium | 18 mg |
| Lactose | 45 mg |
| Total | 200 mg |

According to the usual method, tablets each containing the above components were prepared.

Preparation Example 2

| 6-[3-(3,4-Dimethoxybenzyl)amino-2-hydroxypropoxy]-carbostyril | 500 mg |
|---|---|
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 100 ml |

The above parabens, sodium metabisulfite and sodium chloride were dissolved in the above distilled water at 80° C. with stirring. The obtained solution was cooled to 40° C. The compound of the present invention, polyethylene glycol and polyoxyethylene sorbitan monooleate were dissolved successively in the solution and thereto was added the distilled water for injection to adjust to the final volume. The obtained solution was sterilized by filtration with a suitable filter paper and each 1 ml was poured into an ample to prepare injections.

We claim:

1. A method for treating thrombosis comprising administering to a subject an anti-thrombotic effective amount of a carbostyril derivative of the formula:

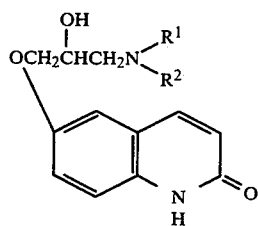

wherein $R^1$ represents hydrogen or a lower alkyl group optionally having a hydroxy group as a substituent;

$R^2$ represents a phenyl(lower alkyl) group optionally having 1-3 substituents selected from the group consisting of a lower alkoxy group and a halogen atom on the phenyl ring; a pyridyl(lower alkyl) group; and a group of the formula —A—NR³R⁴, wherein A represents a lower alkylene group, and wherein $R^3$ and $R^4$, which are the same or different, represent a lower alkyl group or phenyl group; or a salt of said carbostyril derivative.

2. The method for treating thrombosis of claim 1, wherein said method involves inhibiting platelet aggregation.

3. The method for treating thrombosis of claim 1, wherein the carbostyril derivative is 6-[3-(3-methoxybenzyl)amino-2-hydroxypropoxy]carbostyril.

4. The method for treating thrombosis of claim 1, wherein the carbostyril derivatives 6-[3-(3,4-dimethoxybenzyl)amino-2-hydroxypropoxy]carbostyril.

5. The method for treating thrombosis of claim 2, wherein the carbostyril derivative is 6-[3-(3-methoxybenzyl)amino-2-hydroxypropoxy]carbostyril.

6. The method for treating thrombosis of claim 2, wherein the carbostyril derivative is 6-[3-(3,4-dimethoxybenzyl)amino-2-hydroxypropoxy]carbostyril.

7. The method for treating thrombosis of claim 1, wherein $R^2$ is a phenyl(lower alkyl) group optionally having 1-3 substituents selected from the group consisting of a lower alkoxy group and a halogen atom on the phenyl ring.

8. The method for treating thrombosis of claim 7, wherein said method involved inhibiting platelet aggregation.

9. A method for dissociating platelet aggregation comprising administering to subject a platelet aggregation dissociation effective amount of a .carbostyril derivative of the formula:

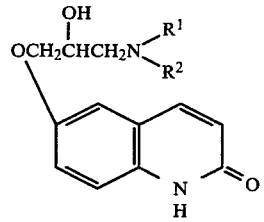

wherein $R^1$ represents hydrogen or a lower alkyl group optionally having a hydroxy group as a substituent;

$R^2$ represents a phenyl(lower alkyl) group optionally having 1-3 substituents selected from the group consisting of a lower alkoxy group and a halogen atom on the phenyl ring; a pyridyl(lower alkyl) group; and a group of the formula —A—NR³R⁴, wherein A represents a lower alkylene group; and wherein $R^3$ and $R^4$, which are the same or different, represent a lower alkyl group or phenyl group; or a salt of said carbostyril derivative.

10. The method for dissociating platelet aggregation of claim 9, wherein the carbostyril derivative is 6-[3-(3-methoxybenzyl)amino-2-hydroxypropoxy]carbostyril 11. The method for dissociating platelet aggregation of claim 9, wherein the carbostyril derivative is 6-[3-(3,4-dimethoxybenzyl)amino-2-hydroxypropoxy]carbostyril.

12. The method for dissociating platelet aggregation of claim 9, wherein $R^2$ is a phenyl(lower alkyl) group optionally having 1-3 substituents selected from the group consisting of a lower alkoxy group and a halogen atom on the phenyl ring.

13. The method according to any one of claims 1, 2, or 9, wherein the effective amount of the carbostyril derivative is in the range of about 0.1 to 10 mg per kg of body weight per day.

* * * * *